United States Patent [19]

Hiti et al.

[11] Patent Number: 5,350,518
[45] Date of Patent: Sep. 27, 1994

[54] MAGNESIUM ELECTRODE

[75] Inventors: John Hiti, Danvers; Chung C. Young, Weston, both of Mass.

[73] Assignee: Nova Biomedical Corporation, Waltham, Mass.

[21] Appl. No.: 105,340

[22] Filed: Aug. 11, 1993

Related U.S. Application Data

[63] Continuation of Ser. No. 675,407, Mar. 26, 1991, abandoned, which is a continuation-in-part of Ser. No. 671,053, Mar. 18, 1991, abandoned.

[51] Int. Cl.$^5$ .................................................. B01D 71/06
[52] U.S. Cl. .................................. 210/638; 210/490; 210/500.27
[58] Field of Search ................ 204/418; 210/638, 645, 210/490, 500.25, 500.27

[56] References Cited

U.S. PATENT DOCUMENTS

| | | | |
|---|---|---|---|
| 3,483,112 | 12/1969 | Ross | 204/195 |
| 3,691,047 | 9/1972 | Ross et al. | 204/195 |
| 4,115,209 | 9/1978 | Freiser et al. | 204/195 M X |
| 4,168,219 | 9/1979 | Hiiro et al. | 204/195 M |
| 4,214,968 | 7/1980 | Battaglia et al. | 204/195 |
| 4,233,144 | 11/1980 | Pace et al. | 204/195 B |
| 4,454,007 | 6/1984 | Pace | 204/418 X |
| 4,619,754 | 10/1986 | Niki et al. | 204/403 X |
| 4,773,970 | 9/1988 | Purbrick et al. | 204/418 X |
| 4,853,090 | 8/1989 | Daniel et al. | 204/418 X |
| 4,861,455 | 8/1989 | Sugihara et al. | 204/418 |
| 4,933,070 | 6/1990 | Toner et al. | 204/418 |

FOREIGN PATENT DOCUMENTS

| | | |
|---|---|---|
| 989441 | 11/1984 | U.S.S.R. |
| 1124214 | 11/1984 | U.S.S.R. |

OTHER PUBLICATIONS

Prabhu et al., Anal. Chem., 59(8), pp. 1074–1078 (1987).
Sugihara et al., Chem. Letters, 1987(12), pp. 2391–2392.
Chem. Abstract 100:78981y, Petrukhin et al., Zh. Anal. Khim., 38(11), pp. 1992–1997 (1983).
Chem. Abstract 106:95038n, Rogatinskaya et al., Ionnyi Obmen Ionometriya, 5, pp. 188–194 (1986).

*Primary Examiner*—Frank Spear
*Attorney, Agent, or Firm*—Fish & Richardson

[57] ABSTRACT

The magnesium ion content of a sample is determined by contacting the sample with a magnesium ion selective membrane including a 1,10-phenanthroline having an H group at positions 2 and 9. Examples of preferred 1,10-phenanthrolines include 4,7-diphenyl-1,10-phenanthroline, N-dodecyl-N-methyl-1,10-phenanthroline-4-carboxamide, 4-undecyl-1,10-phenanthroline, 4,7-diundecyl-1,10-phenanthroline and 5-nonyl-1,10-phenanthroline-4-carboxylate.

82 Claims, 1 Drawing Sheet

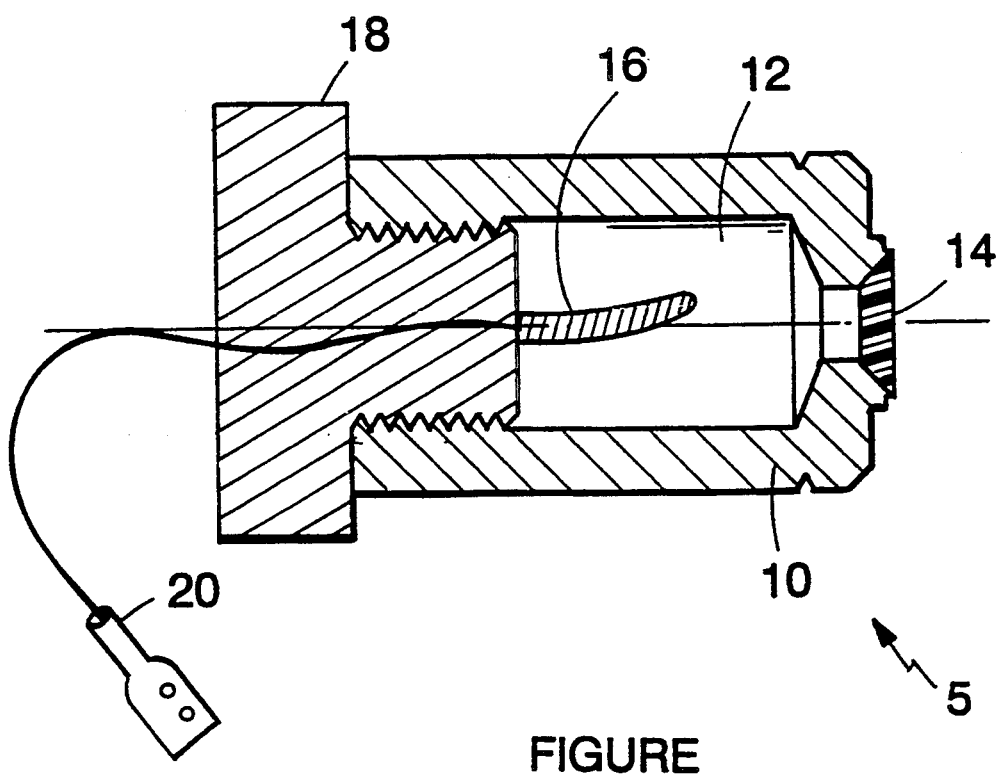
FIGURE

MAGNESIUM ELECTRODE

This is a continuation of application Ser. No. 07/675,407, filed Mar. 26, 1991, now abandoned, which is a continuation-in-part of U.S. Ser. No. 07/671,053, filed Mar. 18, 1991, now abandoned.

BACKGROUND OF THE INVENTION

This invention relates to magnesium selective membranes, e.g., membranes used in magnesium ion measuring electrodes.

1,10-Phenanthroline has the following structure:

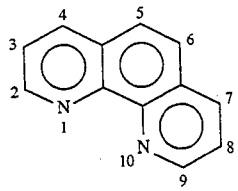

SUMMARY OF THE INVENTION

In general, the invention features a magnesium ion selective membrane including, as a magnesium ion selective compound, a 1,10-phenanthroline.

In preferred embodiments each of the C atoms at positions 2–9 of the 1,10-phenanthroline is bonded, by the bond which does not participate in the fused ring structure, to an H. In other preferred embodiments each of the C atoms at positions 2 and 9 of the 1,10-phenanthroline is bonded, by the bond which does not participate in the fused ring structure, to an H, and each of the C atoms at positions 3–8 of the 1,10-phenanthroline is substituted at the bond which does not participate in the fused ring structure.

In yet other preferred embodiments the 1,10-phenanthroline has the formula

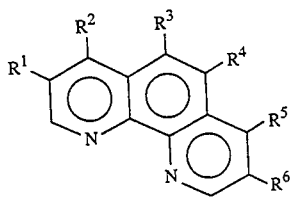

wherein each $R^1$–$R^6$ is any of:
H;
any of F, Cl, Br, I, $NO_2$, CN, or $CF_3$;
$C_{1-18}$ alkyl;
$C_{1-18}$ aryl;
$C_{1-18}$ alkenyl; or
$(CH_2)_m Y$, wherein m is 0 or an integer between 1 and 4 inclusive, Y is any of $-OR^7$, $-NR^7R^8$, $-O-COR^7$, $-NR^7COR^8$, $-COR^7$, $-COOR^7$, $-SO_3R^7$, $-OSiR^7R^8R^9$, wherein each $R^7$, $R^8$, and $R^9$ is any of H, alkyl, branched alkyl, aryl, or substituted aryl; or
$C_n-R^{10}-R^{11}$, wherein n is 0 or an integer between 1 and 17 inclusive, $R^{10}$ is C, N, NCO, or $CH_2-Z-CH_2$ wherein Z is any of O, NH, S, OCO, or CO, $R^{11}$ is

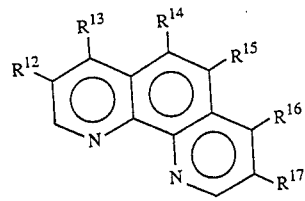

and $R^{11}$ is linked to $R^{10}$ at any of positions 3, 4, 5, 6, 7, or 8 of $R^{11}$, $R^{12}$–$R^{17}$ are any of H, $C_{1-18}$ alkyl, $C_{1-18}$ aryl, or deleted, provided that if $R^{11}$ is linked to $R^{10}$ at position 3 of $R^{11}$ then $R^{12}$ is deleted, if $R^{11}$ is linked to $R^{10}$ at position 4 of $R^{11}$ then $R^{13}$ is deleted, if $R^{11}$ is linked to $R^{10}$ at position 5 of $R^{11}$ then $R^{14}$ is deleted, if $R^{11}$ is linked to $R^{10}$ at position 6 of $R^{11}$ then $R^{15}$ is deleted, if $R^{11}$ is linked to $R^{10}$ at position 7 of $R^{11}$ then $R^{16}$ is deleted, if $R^{11}$ is linked to $R^{10}$ at position 8 of $R^{11}$ then $R^{17}$ is deleted, provided that one of $R^1$–$R^6$ is other than H and that each of the C atoms at positions 2 and 9 of the 1,10-phenanthroline is bonded, by the bond which does not participate in the fused ring structure, to an H.

In yet other preferred embodiments the 1,10-phenanthroline has the formula

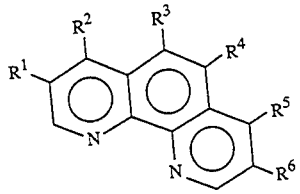

wherein each $R^1$–$R^6$ is any of:
H;
any of F, Cl, Br, I, $NO_2$, CN, or $CF_3$;
$C_{1-18}$ alkyl;
$C_{1-18}$ aryl;
$C_{1-18}$ alkenyl; or
$(CH_2)_m Y$, wherein m is 0 or an integer between 1 and 4 inclusive, Y is any of $-OR^7$, $-NR^7R^8$, $-O-COR^7$, $-NR^7COR^8$, $-COR^7$, $-COOR^7$, $-SO_3R^7$, $-OSiR^7R^8R^9$, wherein each $R^7$, $R^8$, and $R^9$ are any of H, alkyl, branched alkyl, aryl, or substituted aryl; or
provided that one of $R^1$–$R^6$ is other than H and that each of the C atoms at positions 2 and 9 of the 1,10-phenanthroline is bonded, by the bond which does not participate in the fused ring structure, to an H.

Preferred embodiments include those in which $R^1$–$R^6$ include a total of at least 6 carbon atoms; $R^1$–$R^6$ include a total of at least eleven carbon atoms; $R^1$–$R^6$ include a total of 108 C and hetero-atoms; $R^1$ is an alkyl or aryl group having between 1 and 18 carbon atoms; $R^2$ is an alkyl or aryl group having between 1 and 18 carbon atoms; $R^3$ is an alkyl or aryl group having between 1 and 18 carbon atoms; $R^4$ is an alkyl or aryl group having between 1 and 18 carbon atoms; $R^5$ is an alkyl or aryl group having between 1 and 18 carbon atoms; $R^6$ is an alkyl or aryl group having between 1 and 18 carbon atoms.

Other preferred embodiments include those in which the magnesium selective compound is 4,7-diphenyl-1,10-phenanthroline; N-dodecyl-N-methyl-1,10-phenanthroline-4-carboxamide; 4-undecyl-1,10-phenanthroline; 4,7-diundecyl-1,10-phenanthroline; and 5-nonyl-1,10-phenanthroline-4-carboxylate.

In other preferred embodiments the membrane further includes a plasticizer, e.g., 2-nitrophenyl octyl ether.

In another aspect, the invention features an electrode cap or an electrode for determining the magnesium ion content of a liquid sample, e.g., a biological fluid, e.g., blood, plasma or serum. Preferably, the sample is undiluted. Preferred embodiments include, as a magnesium selective membrane, any of the magnesium selective membranes described above.

In another aspect the invention features a method of determining the magnesium ion content of a sample e.g., a biological fluid, e.g., blood, or serum, including contacting said sample with an electrode which includes one of the selective membranes described above and reading the output of the electrode. Preferably, the sample is undiluted.

In preferred embodiments the sample is contacted with the selective membrane generating a potential which is proportional to the logarithm of the magnesium concentration in the sample.

In another aspect, the invention features a method of making a magnesium ion selective membrane including adding one of the magnesium ion selective compounds described above to a membrane.

In preferred embodiments, groups $R^1$–$R^6$ provide sufficient lipophilicity to the compound so that it is not substantially extracted from the membrane into a sample, e.g., serum, e.g., undiluted serum. Preferably $R^1$–$R^6$ provide sufficient lipophilicity to the compound so that a sufficient amount of the compound is retained in the membrane throughout its useful life (which may be only one or a few analyses in the case of a disposable membrane or electrode, or as many as 10–100, several hundreds, or even thousands of analyses in other embodiments). Sufficient retentions means sufficient to provide a Nernstian response to a given level of magnesium ions in a sample despite repeated exposure to samples of a biological fluid, e.g., blood, or undiluted human serum. Generally, sufficient lipophilicity is obtained if $R^1$–$R^6$ include a total of at least 6, preferably at least 11, carbon atoms.

In another aspect the invention includes the compounds N-methyl-N-dodecyl-1,10-phenanthroline-4-carboxamide, and 5-nonyl 1,10-phenanthroline-4-carboxylate.

In another aspect the invention features a method of sequestering the $Mg^{2+}$ ions in a sample which includes contacting the sample with a 1,10-phenanthroline which is complexed e.g., by a covalent or ionic linkage, or by hydrophobic interactions, with a substrate, e.g., a solid matrix, e.g., a filter, or a particle, e.g., a polyethylene, a polystyrene, or polyacrylamide sphere.

The electrodes of the invention have good selectivity for magnesium ions, even in the presence of calcium ions. The electrodes provide accurate and consistent measurements of the magnesium ion content of liquids, including undiluted serum and whole blood samples. The electrodes, and membranes, are durable, and can be used repeatedly, e.g., hundreds of analyses in some applications, before needing replacement.

Other objects, features, and advantages of this invention will be apparent to those skilled in the art from the following detailed description of the preferred embodiments thereof, and from the claims.

DESCRIPTION OF THE PREFERRED EMBODIMENT

The FIGURE is a sectional view of an electrode embodying the invention.

Structure

The electrode assembly 5 includes a plastic, preferably PVC, cap 10, with lumen 12, and membrane 14. Internal reference electrode 16 is positioned within lumen 12 by electrode frame 18 and is in electrical contact with lead 20. In a preferred embodiment, membrane 14 is composed of an organic plastic matrix; a plasticizer; an ion excluder; and a 1,10-phenanthroline compound. The membrane materials are all soluble in the volatile solvent tetrahydrofuran.

The plastic matrix e.g., PVC, provides support for the membrane. Sufficient plastic matrix e.g., PVC, should be used to make a strong membrane, but not so much that it interferes with the electrochemical properties of membrane. Most preferably the membrane consists of 25 to 30% PVC by weight.

The plasticizer serves as the solvent for the 1,10-phenanthroline compound. Sufficient plasticizer should be included in the membrane so that it keeps the 1,10-phenanthroline solvated in the membrane, but not so much that a weak membrane is obtained. Preferably, the membrane is 60 to 75% plasticizer by weight. Suitable plasticizers include ethers, esters, and phosphonates. The most preferred plasticizer is 2-nitrophenyl octyl ether, which is available from Fluka, Inc.

The anion excluder provides negative sites which help prevent binding of small anions to the membrane. Preferably the membrane includes 1 to 3% of an anion excluder such as potassium tetrakis(p-chlorophenyl)borate, which is available from Fluka, Inc.

The 1,10-phenanthroline serves as a magnesium ion selective compound. The preferred 1,10-phenanthrolines are those having the formulas described above. The alkyl or aryl groups can include other functionalities, such as —OR, —NR$_2$, —OCOR, —NRCOR, —COR, COOR, —SO$_3$R, and —OSiR$_3$, as described above. Importantly, a sufficient number of carbon atoms should be included in $R^1$–$R^6$ so that the compound is lipophilic. Typically, at least six, and preferably 11 or more carbon atoms are contained in $R^1$–$R^6$. If an insufficient number of carbon atoms are included in the side chains, the compound will be extracted from the membrane into the sample.

Examples of preferred 1,10-phenanthroline derivatives are N-dodecyl-N-methyl-1,10-phenanthroline-4-carboxamide; 4-undecyl-1,10-phenanthroline; 4,7-diundecyl-1,10-phenanthroline; 5-nonyl-1,10-phenanthroline-4-carboxylate; and 4,7-diphenyl-1,10-phenanthroline.

Bulky groups at positions 2 and 9 i.e., group other than H, are undesirable in the compounds of the invention. 2-methyl-1,10-phenanthroline, 2,9-dimethyl-1,10-phenanthroline, and 1,10-phenanthroline-2 METHYL LAURATE all failed to bind $Mg^{2+}$ ions sufficiently for use in the invention.

To make the membrane 14, 125 mg of high molecular weight PVC polymer in powder form (available from Aldrich Chemical Co., catalog no. 18956-1) is dissolved in 2 ml of tetrahydrofuran. To this solution were then added 300 mg of the solvent plasticizer 2-nitrophenyl octyl ether, 25 mg of the Mg selective ionophore 4-undecyl-1,10-phenanthroline, and 8 mg potassium tetrakis (4-chlorophenyl)borate. The membrane thus formed has the composition of 5.5 wt % ionophore, 4-undecyl-1,10-phenanthroline; 65.5 wt % 2-nitrophenyl octyl ether plasticizer; 27 wt % matrix poly(vinyl)chloride; and approximately 2 wt % potassium tetrakis (4-chlorophenyl)borate.

The membrane is made by depositing the solution on the tip of cap 10, and allowing the solvent to evaporate. Membranes thus formed demonstrate good mechanical strength, durability, and analytical performance. The slope of the logarithm of $Mg^{+2}$ concentration vs. electrical potential was near Nernstian, selectivity for $Mg^{+2}$ over $Ca^{+2}$ was excellent.

The electrodes of the invention may incorporate an integral reference electrode. In such embodiments the electrode includes within its structure substantially all of the components needed for making a potentiometric determination with (preferably) the exception of a second reference electrode, the potential-indicating device and associated wiring, so that in use the user merely needs to provide for contacting the sample with the ion-selective membrane, e.g., by application of a small quantity of the sample to be analyzed (on the order of $<100$ μl) thereto and making the necessary electrical connections. Automated dispensers for applying controlled amounts of sample to the electrode at the appropriate location are known and any such dispenser or for that matter careful manual dispensing, may be used to contact the sample with the electrode. Alternatively, the electrode may actually be immersed in or contacted with the surface of the solution under analysis.

The substituted 1,10-phenanthroline compounds are synthesized by standard techniques known to those skilled in the art. For example, the synthesis of 4- and 4,7-substituted 1,10-phenanthrolines are described in Lund et al., J. Chem. Eng. Data, 26: 227-29 (1981), hereby incorporated by reference. Methyl groups can provide a handle for the attachment of the desired sidechain in the synthesis of other 1,10-phenanthroline derivatives, and methyl substituted 1,10-phenanthrolines are commercially available. For example, 4-methyl, 5-methyl, 6-methyl, 7-methyl, 3,6-dimethyl, 5,7-dimethyl, 4,7-dimethyl, and 5,6-dimethyl-1,10-phenanthroline are all available from Aldrich Chemical Co.

Specific examples of the synthesis of 1,10-phenanthroline derivatives follow.

N-Dodecyl-N-methyl 1,10-phenanthroline-4-carboxamide was synthesized in the following steps. The first step in the synthesis was the production of 1,10-phenanthroline-4-carboxylic acid. 0.94 g (0.005 moles) of 4-methyl-1,10-phenanthroline, 2.96 g (0.027 moles) selenium (IV) oxide, 3.1 ml of deionized water, and 103 ml of p-dioxane, were mixed together, refluxed for 1¾ hr, then hot filtered through filter-aid (e.g., diatomaceous earth) and concentrated. The residue was dissolved in 70% nitric acid, heated to reflux, refluxed for 2 hr., cooled, and poured over ice. The precipitated solid was filtered, and then dried in a vacuum oven to produce 0.57 g of a white solid (1,10-phenanthroline-4-carboxylic acid) with a melting point of 228° C. dec. TLC showed a small amount of less polar material. The yield was 52%.

In steps 2 and 3, 0.57 g (0.0025 moles) of 1,10-phenanthroline-4-carboxylic acid was slurried in 19 ml (0.26 moles) of thionyl chloride and refluxed for 3 hr. The reaction mixture was concentrated on a roto-vap and the residue slurried in 50 ml chloroform. 0.7 g (0.0035 moles) of N-methyldodecylamine and 1 ml (0.007 moles) of triethylamine dissolved in 25 ml chloroform were added dropwise to the acid chloride. The resulting mixture was stirred at room temperature overnight, concentrated, the residue slurried in ether and washed 2 times with 100 ml of saturated NaCl. The organic layer was dried over sodium sulfate, filtered, and the filtrate concentrated. The residue was chromatographed on neutral alumina, eluting with 5% methanol:ether. The appropriate fractions were concentrated, the residue dissolved in ether, filtered through a 0.45 μm filter, concentrated, then pumped down under high vacuum overnight to yield 0.4 g of orange oil (N-dodecyl-N methyl 1,10-phenanthroline-4-carboxamide). TLC shows a trace of less polar material. IR analysis was consistent with the expected structure. The yield was 38%.

5-nonyl 1,10-phenanthroline carboxylate was synthesized as follows: 1 equivalent of 1,10-phenanthroline-4-carbonyl chloride (prepared as described above in the discussion of N-dodecyl-N-methy-1,10-phenanthroline-4-carboxamide) was reacted with 1 equivalent of 5-nonanol in the presence of pyridine to give the desired product, 5-nonyl-1,10-phenanthroline-4-carboxylate.

4-Undecyl-1,10-phenanthroline was synthesized in the following four steps. The first step was the synthesis of 1-tetradecen-3-ol. 100 ml (0.1 moles) of vinyl magnesium bromide in THF was cannulated into a flask under $N_2$, chilled in an ice bath, and 12.29 g (0.0667 moles) of dodecyl aldehyde added dropwise. The reaction mixture was stirred at room temperature overnight, poured into HCl and ice, and extracted with 3×200 ml ether. The combined organic layers were washed 3 times with 100 ml of saturated sodium bicarbonate and 3 times with 30 ml of deionized water. The organic layer was dried over magnesium sulfate, filtered, and the filtrate concentrated. The residue was chromatographed on 253.6 g silica gel, eluting with hexanes, 10% EtOAc(ethyl acetate):hexanes, then 20% EtOAc:hexanes. The appropriate fractions were concentrated and the concentrate Kugelrohr distilled under high vacuum to yield 4.1 g of clear colorless liquid with a bp of 70°-80° C./0.006 mm. TLC shows less polar spots. IR analysis was consistent with the expected structure. The yield was 28%.

The second step was the synthesis of 1-tetradecen-3-one from 1-tetradecen-3-ol. 6.00 g (0.06 moles) of chromium (VI) trioxide was added to 9.7 ml (0.12 moles) of pyridine dissolved in 150 ml of dichloromethane and stirred at room temperature for 50 min. The reaction mixture turned deep red. 2.15 g (0.01 moles) of 1-tetradecen-3-ol in 20 ml dichloromethane was added quickly. A solid precipitated from solution. The reaction mixture was stirred at room temperature for 50 min., the solution decanted, and the precipitate washed with dichloromethane. The combined organics were washed 2 times with 100 ml of 10% NaOH, 2 times with 100 ml of 10% HCl, 2 times with 100 ml of saturated sodium bicarbonate, and 1 time with 100 ml of deionized water. The organic layer was dried over sodium sulfate, filtered, and the filtrate concentrated. The residue was Kugelrohr distilled under high vacuum to yield 1.8 g clear colorless liquid bp 60°-70° C./0.009 mm. TLC showed a small amount of more and less polar spots. IR analysis was consistent with the expected structure. The yield was 84%.

The third step was the synthesis of 8-aminoquinoline. 39.76 g (0.23 moles) of 8-nitroquinoline, 0.54 g of 5% palladium on carbon, and 300 ml of 95% ethanol were shaken together under $H_2$. After the requisite amount of hydrogen was taken up, the reaction mixture was filtered and the filtrate concentrated. The residue was Kugelrohr distilled under high vacuum to yield 31.6 g of yellow solid with a mp of 64°–65° C., and a bp of 65°–75° C./0.01 mm with a TLC shows a small amount of a more polar material. The yield was 96%.

In the fourth step 8-aminoquinoline was reacted with 1-tetradecen-3-one to yield 4-n-undecyl-1,10-phenanthroline. 3.6 g (0.025 moles) of 8-aminoquinoline, 0.54 g (0.0039 moles) of zinc chloride, 7.5 g (0.033 moles) of 3-nitrobenzene sulfonic acid sodium salt, and 10 ml (0.12 moles) of 37% HCl were slurried in 124 ml EtOH. 5.26 g (0.025 moles) of 1-tetradecen-3-one in 24 ml EtOH and added dropwise to the slurry. The reaction mixture was refluxed for 19 hr, cooled, concentrated and made basic with ammonium hydroxide. The aqueous layer was extracted 2 times with 100 ml of dichloromethane. The organic layers were dried over sodium sulfate, filtered, and the filtrate concentrated. The residue in ca. 100 ml of EtOH, 200 ml of 10% HCl added, and the reaction cooled at 4° C. for approximately 16 hours. The resulting solid was filtered, dissolved in EtOH, concentrated ammonium hydroxide added, and placed at 0° C. The resulting solid was filtered, air dried and recrystallized from hexanes to yield 1.7 g tan solid with a mp of 64°–65° C. TLC showed one spot IR analysis was consistent with the expected structure. The yield was 19%

4,7-Diundecyl-1,10-phenanthroline was synthesized as follows: 2.7 g (0.025 moles) of 1,2-phenylenediamine was dissolved in 200 ml ethanol, and 15.0 g (0.067 moles) of 3-nitrobenzene sulfonic acid sodium salt, 0.54 g (0.0039 moles) zinc chloride, and 10 ml of 37% HCl added. The mixture was heated 60° C., and 4.8 g (0.021 moles) of 1-pentadecen-4-one in 26 ml ethanol added dropwise. Upon completion of the addition the reaction was refluxed overnight. The reaction was cooled, concentrated, and then made basic with ammonium hydroxide. The aqueous layer was extracted 2 times with 100 ml dichloromethane. The organic layers were dried over sodium sulfate, filtered, and the filtrate concentrated. The residue was dissolved in ca. 100 ml of EtOH. 300 ml of 10% HCl were added and the mixture placed at 4° C. for approximately 16 hours. The resulting solid was filtered, dissolved in EtOH, concentrated ammonium hydroxide added, then placed at 0° C. for approximately 6 hours. The resulting solid was filtered, air dried, and recrystallized from hexanes to yield 1.7 g of tan solid with a melting point of 95°–97° C. TLC showed a trace of less polar material. IR analysis was consistent with the expected structure. The yield was 22%.

Use

In ion specific electrode measurements the electrodes must be calibrated prior to their use in an analysis. In all cases, at least a two point calibration is performed; in this instance, two internal standards were used. One standard, B, contained 1.0 mmol $Mg^{+2}$ while a second, A, contained 0.5 mmol $Mg^{+2}$ Prior to an analysis, the electrode is calibrated with the two standards. With each standard, the electrode develops an electrical potential proportional to the logarithm of the concentration of $Mg^{+2}$. According to the Nernst equation, the logarithm of concentration and potential are linearly related: the difference in potential for a ten fold change in concentration should be 29.6 mv at 25° C. Measurement of $Mg^{+2}$ in an unknown is performed by comparing the potential developed by the electrode in the sample (either an aqueous solution or serum) with the linear calibration graph.

In use, the lumen 12 of electrode cap 5 is filled with an internal filling solution, e.g., 60 mmol $MgCl_2$ and reference electrode 16, preferably a silver wire coated with AgCl, is inserted into the filling solution in the lumen 12. Varying concentrations of $Mg^{2+}$ in the sample result in varying potential between the tip of the reference electrode 16 and the membrane 14.

The compounds, membranes, electrode caps, and electrodes of the invention can be incorporated into an automated sample analyzer, e.g., a Nova STAT analyzer (Nova Biomedical, Waltham, Mass. 02254).

Automated sample analyzers which use capillary sampling devices generally require a capillary tube with a delivery volume above some minimum level. The minimum level is characteristic of the instrument and can be determined by one skilled in the art. Capillary tubes can be adapted to the instrument with Nova capillary adapters.

Correct sample handling is critical to ensure that the values obtained accurately reflect the in vivo state. Ensure that all samples have been obtained and stored following consistent, clinically accepted protocols. It is particularly important to ensure that samples are well mixed before introduction into the analyzer. Samples analyzed for magnesium ions should be anaerobic.

Sodium and lithium heparin are the recommended anticoagulants. EDTA, citrate, oxalate, or sodium fluoride are not recommended for use during electrolyte analysis. Depending on the amount of heparin used in the collection syringe and whether it is filled to capacity with blood, heparin concentrations of 20 I.U. per ml to over 100 I.U. per ml heparin may result.

Phosphate can interfere with $Mg^{+2}$ determinations. At a level of 1 mmol/L $Mg^{+2}$, a level of 5 mmol/L Phosphate decreased the observed $Mg^{+2}$ by 20%.

Typical values for ionized magnesium in whole blood, serum, or plasma are within the range of 0.45–0.60 mmol/L. Each laboratory should, however, establish and maintain its own reference values.

Other embodiments are within the following claims.

We claim:

1. A method of determining the magnesium ion content of a sample comprising contacting said sample with an electrode comprising a magnesium ion selective membrane comprising, as a magnesium selective compound, a 1,10-phenanthroline having an H group at positions 2 and 9, and reading the output of said electrode.

2. The method of claim 1, wherein said sample is biological fluid.

3. The method of claim 2, wherein said sample is undiluted plasma.

4. The method of claim 1, wherein said sample is whole blood.

5. The method of claim 1, wherein said sample is serum.

6. The method of claim 5, wherein said sample is undiluted serum.

7. The method of claim 4, wherein said sample is contacted with said selective membrane, and said output corresponds to a change in potential.

8. The method of claim 1, wherein each of the C atoms at positions 3–8 of said 1,10-phenanthroline is bonded, by the bond which does not participate in the fused ring structure, to an H.

9. The method of claim 1, wherein each of the C atoms at positions 3–8 of said 1,10-phenanthroline is substituted at the bond which does not participate in the fused ring structure.

10. The method of claim 1, wherein said 1,10-phenanthroline has the formula

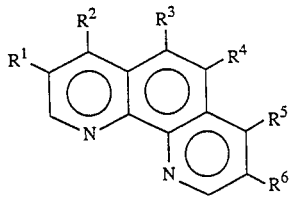

wherein each $R^1$–$R^6$ is any of:
H;
any of F, Cl, Br, I, $NO_2$, CN, or $CF_3$;
$C_{1-18}$ alkyl;
$C_{1-18}$ aryl;
$C_{1-18}$ alkenyl; or
$(CH_2)_mY$, wherein m is 0 or an integer between 1 and 4 inclusive Y is any of —$OR^7$, —$NR^7R^8$, —O-$COR^7$, —$NR^7COR^8$, —$COR^7$, —$COOR^7$, $SO_3R^7$, $OSiR^7R^8R^9$, wherein each $R^7$, $R^8$, and $R^9$ are any of H, alkyl, branched alkyl, aryl, or substituted aryl; or
$C_n$—$R^{10}$—$R^{11}$, wherein n is 0 or an integer between 1 and 17 inclusive, $R^{10}$ is C, N, NCO, or $CH_2$—Z—$CH_2$ wherein Z is any of O, NH, S, OCO, or CO, $R^{11}$ is

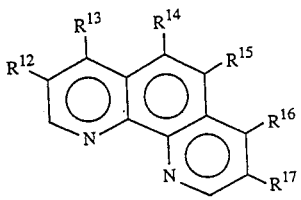

and $R^{11}$ is linked to $R^{10}$ at any of positions 3, 4, 5, 6, 7, or 8 of $R^{11}$, $R^{12}$–$R^{17}$ are any of H, $C_{1-18}$ alkyl, $C_{1-18}$ aryl, or deleted, provided that if $R^{11}$ is linked to $R^{10}$ at position 3 of $R^{11}$ then $R^{12}$ is deleted, if $R^{11}$ is linked to $R^{10}$ at position 4 of $R^{11}$ then $R^{13}$ is deleted, if $R^{11}$ is linked to $R^{10}$ at position 5 of $R^{11}$ then $R^{14}$ is deleted, if $R^{11}$ is linked to $R^{10}$ at position 6 of $R^{11}$ then $R^{15}$ is deleted, if $R^{11}$ is linked to $R^{10}$ at position 7 of $R^{11}$ then $R^{16}$ is deleted, if $R^{11}$ is linked to $R^{10}$ at position 8 of $R^{11}$ then $R^{17}$ is deleted, provided that one of $R^1$–$R^6$ is other than H and that each of the C atoms at positions 2 and 9 of the 1,10-phenanthroline is bonded, by the bond which does not participate in the fused ring structure, to an H.

11. The method of claim 1, wherein said 1,10-phenanthroline has the formula

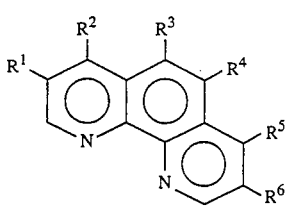

wherein each $R^1$–$R^6$ is any of:
H;
any of F, Cl, Br, I, $NO_2$, CN, or $CF_3$;
$C_{1-18}$ alkyl;
$C_{1-18}$ aryl;
$C_{1-18}$ alkenyl; or
$(CH_2)_mY$, wherein m is 0 or an integer between 1 and 4 inclusive, Y is any of —$OR^7$, —$NR^7R^8$, —O-$COR^7$, —$NR^7COR^8$, —$COR^7$, —$COOR^7$, $SO_3R^7$, $OSiR^7R^8R^9$, wherein each $R^7$, $R^8$, and $R^9$ are any of H, alkyl, branched alkyl, aryl, or substituted aryl; provided that one of $R^1$–$R^6$ is other than H and that each of the C atoms at positions 2 and 9 of said 1,10-phenanthroline is bonded, by the bond which does not participate in the fused ring structure, to an H.

12. The method of claim 11, wherein $R^1$–$R^6$ include a total of at least 6 carbon atoms.

13. The method of claim 11, wherein $R^1$–$R^6$ include a total of at least eleven carbon atoms.

14. The method of claim 11, wherein $R^1$ is an alkyl or aryl group having between 1 and 18 carbon atoms.

15. The method of claim 11, wherein $R^2$ is an alkyl or aryl group having between 1 and 18 carbon atoms.

16. The method of claim 11, wherein $R^3$ is an alkyl or aryl group having between 1 and 18 carbon atoms.

17. The method of claim 11, wherein $R^4$ is an alkyl or aryl group having between 1 and 18 carbon atoms.

18. The method of claim 11, wherein $R^5$ is an alkyl or aryl group having between 1 and 18 carbon atoms.

19. The method of claim 11, wherein $R^6$ is an alkyl or aryl group having between 1 and 18 carbon atoms.

20. The method of claim 11, wherein said membrane further comprises a plasticizer.

21. The method of claim 11, wherein said membrane further comprises a matrix.

22. The method of claim 21, wherein said matrix comprises PVC.

23. The method of claim 11, wherein said membrane further comprises an ion excluder.

24. The method of claim 1 wherein said compound is 4,7-diphenyl-1,10-phenanthroline.

25. The method of claim 1, wherein said compound is N-dodecyl-N-methyl-1,10-phenanthroline-4-carboxamide.

26. The method of claim 1, wherein said compound is 4-undecyl-1,10-phenanthroline.

27. The method of claim 1, wherein said compound is 4,7-diundecyl-1,10-phenanthroline.

28. The method of claim 1, wherein said compound is 5-nonyl 1,10-phenanthroline-4-carboxylate.

29. A method of making a magnesium ion selective membrane comprising adding, as a magnesium selective compound, a 1,10-phenanthroline having an H group at positions 2 and 9, to a membrane.

30. The method of claim 29, wherein each of the C atoms at positions 3–8 of said 1,10 phenanthrolines is bonded, by the bond which does not participate in the fused ring structure, to an H.

31. The method of claim 29, wherein each of the C atoms at positions 3–8 of said 1,10-phenanthroline is substituted at the bond which does not participate in the fused ring structure.

32. The method of claim 29, wherein said 1,10-phenanthroline has the formula

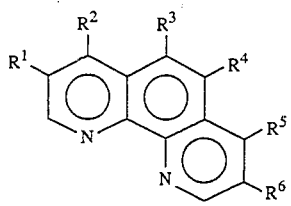

wherein each $R^1$–$R^6$ is any of:
H;
any of F, Cl, Br, I, $NO_2$, CN, or $CF_3$;
$C_{1-18}$ alkyl;
$C_{1-18}$ aryl;
$C_{1-18}$ alkenyl; or
$(CH_2)_m Y$, wherein m is 0 or an integer between 1 and 4 inclusive, Y is any of $-OR^7$, $-NR^7R^8$, $-OCOR^7$, $-NR^7COR^8$, $-COR^7$, $-COOR^7$, $SO_3R^7$, $OSiR^7R^8R^9$, wherein each $R^7$, $R^8$, and $R^9$ are any of H, alkyl, branched alkyl, aryl, or substituted aryl; or
$C_n-R^{10}-R^{11}$, wherein n is 0 or an integer between 1 and 17 inclusive, $R^{10}$ is C, N, NCO, or $CH_2-Z-CH_2$ wherein Z is any of O, NH, S, OCO, or CO, $R^{11}$ is

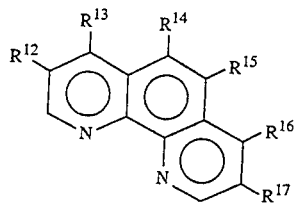

and $R^{11}$ is linked to $R^{10}$ at any of positions 3, 4, 5, 6, 7, or 8 of $R^{11}$, $R^{12}$–$R^{17}$ are any of H, $C_{1-18}$ alkyl, $C_{1-18}$ aryl, or deleted, provided that if $R^{11}$ is linked to $R^{10}$ at position 3 of $R^{11}$ then $R^{12}$ is deleted, if $R^{11}$ is linked to $R^{10}$ at position 4 of $R^{11}$ then $R^{13}$ is deleted, if $R^{11}$ is linked to $R^{10}$ at position 5 of $R^{11}$ then $R^{14}$ is deleted, if $R^{11}$ is linked to $R^{10}$ at position 6 of $R^{11}$ then $R^{15}$ is deleted, if $R^{11}$ is linked to $R^{10}$ at position 7 of $R^{11}$ then $R^{16}$ is deleted, if $R^{11}$ is linked to $R^{10}$ at position 8 of $R^{11}$ then $R^{17}$ is deleted, provided that one of $R^1$–$R^6$ is other than H and that each of the C atoms at positions 2 and 9 of the 1,10-phenanthroline is bonded, by the bond which does not participate in the fused ring structure, to an H.

33. The method of claim 29, wherein said 1,10-phenanthroline has the formula

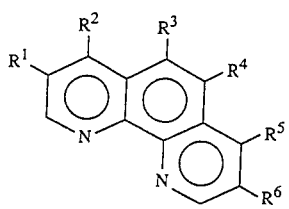

wherein each $R^1$–$R^6$ is any of:
H;
any of F, Cl, Br, I, $NO_2$, CN, or $CF_3$;
$C_{1-18}$ alkyl;
$C_{1-18}$ aryl;
$C_{1-18}$ alkenyl; or
$(CH_2)_m Y$, wherein m is 0 or an integer between 1 and 4 inclusive, Y is any of $-OR^7$, $-NR^7R^8$, $-OCOR^7$, $-NR^7COR^8$, $-COR^7$, $-COOR^7$, $SO_3R^7$, $OSiR^7R^8R^9$, wherein each $R^7$, $R^8$, and $R^9$ are any of H, alkyl, branched alkyl, aryl, or substituted aryl; provided that one of $R^1$–$R^6$ is other than H and that each of the C atoms at positions 2 and 9 of said 1,10-phenanthroline is bonded, by the bond which does not participate in the fused ring structure, to an H.

34. The method of claim 33, wherein $R^1$–$R^6$ include a total of at least 6 carbon atoms.

35. The method of claim 33, wherein $R^1$–$R^6$ include a total of at least eleven carbon atoms.

36. The method of claim 33, wherein $R^1$ is an alkyl or aryl group having between 1 and 18 carbon atoms.

37. The method of claim 33, wherein $R^2$ is an alkyl or aryl group having between 1 and 18 carbon atoms.

38. The method of claim 33, wherein $R^3$ is an alkyl or aryl group having between 1 and 18 carbon atoms.

39. The method of claim 33, wherein $R^4$ is an alkyl or aryl group having between 1 and 18 carbon atoms.

40. The method of claim 33, wherein $R^5$ is an alkyl or aryl group having between 1 and 18 carbon atoms.

41. The method of claim 33, wherein $R^6$ is an alkyl or aryl group having between 1 and 18 carbon atoms.

42. The method of claim 33, wherein said membrane further comprises a plasticizer.

43. The method of claim 33, wherein said membrane further comprises a matrix.

44. The method of claim 43, wherein said matrix comprises PVC.

45. The method of claim 33, wherein said membrane further comprises an ion excluder.

46. The method of claim 29, wherein said compound is 4,7-diphenyl-1,10-phenanthroline.

47. The method of claim 29, wherein said compound is N-dodecyl-N-methyl-1,10-phenanthroline-4-carboxamide.

48. The method of claim 29, wherein said compound is 4-undecyl-1,10-phenanthroline.

49. The method of claim 29, wherein said compound is 4,7-diundecyl-1,10-phenanthroline.

50. The method of claim 29, wherein said compound is 5-nonyl 1,10-phenanthroline-4-carboxylate.

51. A preparation of N-methyl-N-dodecyl-1,10-phenanthroline-4-carboxamide.

52. A preparation of 5-nonyl 1,10-phenanthroline-4-carboxylate.

53. A method of sequestering the $Mg^{++}$ ions in a sample comprising, contacting said sample with a 1,10-phenanthroline having an H group at positions 2 and 9, said 1,10-phenanthroline being linked to a substrate.

54. The method of claim 53, wherein each of the C atoms at positions 3–8 of said 1,10-phenanthroline is bonded, by the bond which does not participate in the fused ring structure, to an H.

55. The method of claim 53, wherein each of the C atoms at positions 3–8 of said 1,10-phenanthroline is substituted at the bond which does not participate in the fused ring structure.

56. The method of claim 53, wherein said 1,10-phenanthroline has the formula

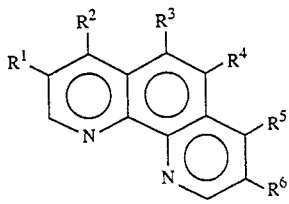

wherein each $R^1$–$R^6$ is any of:
H;
any of F, Cl, Br, I, $NO_2$, CN, or $CF_3$;
$C_{1-18}$ alkyl;
$C_{1-18}$ aryl;
$C_{1-18}$ alkenyl; or
$(CH_2)_m Y$, wherein m is 0 or an integer between 1 and 4 inclusive, Y is any of $-OR^7$, $-NR^7R^8$, $-OCOR^7$, $-NR^7COR^8$, $-COR^7$, $-COOR^7$, $SO_3R^7$, $OSiR^7R^8R^9$, wherein each $R^7$, $R^8$, and $R^9$ are any of H, alkyl, branched alkyl, aryl, or substituted aryl; or
$C_n-R^{10}-R^{11}$, wherein n is 0 or an integer between 1 and 17 inclusive, $R^{10}$ is C, N, NCO, or $CH_2-Z-CH_2$ wherein Z is any of O, NH, S, OCO, or CO, $R^{11}$ is

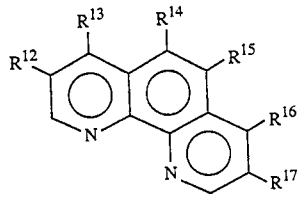

and $R^{11}$ is linked to $R^{10}$ at any of positions 3, 4, 5, 6, 7, or 8 of $R^{11}$, $R^{12}$–$R^{17}$ are any of H, $C_{1-18}$ alkyl, $C_{1-18}$ aryl, or deleted, provided that if $R^{11}$ is linked to $R^{10}$ at position 3 of $R^{11}$ then $R^{12}$ is deleted, if $R^{11}$ is linked to $R^{10}$ at position 4 of $R^{11}$ then $R^{13}$ is deleted, if $R^{11}$ is linked to $R^{10}$ at position 5 of $R^{11}$ then $R^{14}$ is deleted, if $R^{11}$ is linked to $R^{10}$ at position 6 of $R^{11}$ then $R^{15}$ is deleted, if $R^{11}$ is linked to $R^{10}$ at position 7 of $R^{11}$ then $R^{16}$ is deleted, if $R^{11}$ is linked to $R^{10}$ at position 8 of $R^{11}$ then $R^{17}$ is deleted, provided that one of $R^1$–$R^6$ is other than H and that each of the C atoms at positions 2 and 9 of the 1,10-phenanthroline is bonded, by the bond which does not participate in the fused ring structure, to an H.

57. The method of claim 53, wherein said 1,10-phenanthroline has the formula

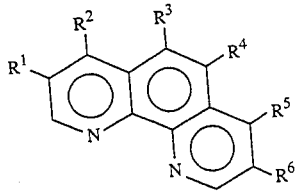

wherein each $R^1$–$R^6$ is any of:
H;
any of F, Cl, Br, I, $NO_2$, CN, or $CF_3$;
$C_{1-18}$ alkyl;
$C_{1-18}$ aryl;
$C_{1-18}$ alkenyl; or
$(CH_2)_m Y$, wherein m is 0 or an integer between 1 and 4 inclusive, Y is any of $-OR^7$, $-NR^7R^8$, $-OCOR^7$, $-NR^7COR^8$, $-COR^7$, $-COOR^7$, $SO_3R^7$, $OSiR^7R^8R^9$, wherein each $R^7$, $R^8$, and $R^9$ are any of H, alkyl, branched alkyl, aryl, or substituted aryl; provided that one of $R^1$–$R^6$ is other than H and that each of the C atoms at positions 2 and 9 of said 1,10-phenanthroline is bonded, by the bond which does not participate in the fused ring structure, to an H.

58. The method of claim 57, wherein $R^1$–$R^6$ include a total of at least 6 carbon atoms.

59. The method of claim 57, wherein $R^1$–$R^6$ include a total of at least eleven carbon atoms.

60. The method of claim 57, wherein $R^1$ is an alkyl or aryl group having between 1 and 18 carbon atoms.

61. The method of claim 57, wherein $R^2$ is an alkyl or aryl group having between 1 and 18 carbon atoms.

62. The method of claim 57, wherein $R^3$ is an alkyl or aryl group having between 1 and 18 carbon atoms.

63. The method of claim 57, wherein $R^4$ is an alkyl or aryl group having between 1 and 18 carbon atoms.

64. The method of claim 57, wherein $R^5$ is an alkyl or aryl group having between 1 and 18 carbon atoms.

65. The method of claim 57, wherein $R^6$ is an alkyl or aryl group having between 1 and 18 carbon atoms.

66. The method of claim 57, wherein said membrane further comprises a plasticizer.

67. The method of claim 57, wherein said membrane further comprises a matrix.

68. The method of claim 67, wherein said matrix comprises PVC.

69. The method of claim 57, wherein said membrane further comprises an ion excluder.

70. The method of claim 53, wherein said compound is 4,7-diphenyl-1,10-phenanthroline.

71. The method of claim 53, wherein said compound is N-dodecyl-N-methyl-1,10-phenanthroline-4-carboxamide.

72. The method of claim 53, wherein said compound is 4-undecyl-1,10-phenanthroline.

73. The method of claim 53, wherein said compound is 4,7-diundecyl-1,10-phenanthroline.

74. The method of claim 53, wherein said compound is 5-nonyl 1,10-phenanthroline-4-carboxylate.

75. A magnesium ion selective membrane comprising, as a magnesium selective compound, N-dodecyl-N-methyl-1,10-phenanthroline-4-carboxamide.

76. An electrode for determining the magnesium ion concentration of a liquid sample comprising the selective membrane of claim 75.

77. A magnesium ion selective membrane comprising, as a magnesium selective compound, 4-undecyl-1,10-phenanthroline.

78. An electrode for determining the magnesium ion concentration of a liquid sample comprising the selective membrane of claim 77.

79. A magnesium ion selective membrane comprising, as a magnesium selective compound, 4,7-diundecyl-1,10-phenanthroline.

80. An electrode for determining the magnesium ion concentration of a liquid sample comprising the selective membrane of claim 79.

81. A magnesium ion selective membrane comprising, as a magnesium selective compound, 5-nonyl 1,10-phenanthroline-4-carboxylate.

82. An electrode for determining the magnesium ion concentration of a liquid sample comprising the selective membrane of claim 81.

* * * * *